US00PP21727P2

(12) United States Plant Patent
Oudolf

(10) Patent No.: US PP21,727 P2
(45) Date of Patent: Feb. 22, 2011

(54) ***CIMICIFUGA* PLANT NAMED 'QUEEN OF SHEBA'**

(50) Latin Name: ***Cimicifuga simplex*×*Cimicifuga racemosa***
Varietal Denomination: Queen of Sheba

(75) Inventor: Petrus Henricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/586,395

(22) Filed: Sep. 21, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—June Hwu
*Assistant Examiner*—Louanne C Krawczewicz Myers
(74) *Attorney, Agent, or Firm*—C. A. Whealy

(57) ABSTRACT

A new and distinct cultivar of *Cimicifuga* plant named 'Queen of Sheba', characterized by its upright and sturdy plant habit; dark-colored leaves; freely flowering habit; white-colored flowers arranged on pendulous racemes; and good garden performance.

2 Drawing Sheets

Botanical designation: *Cimicifuga simplex*×*Cimicifuga racemosa.*

Cultivar denomination: 'QUEEN OF SHEBA'.

BACKGROUND OF THE INVENTION

The present invention relates to a new and distinct cultivar of *Cimicifuga* plant, botanically known as *Cimicifuga simplex*×*Cimicifuga racemosa* and hereinafter referred to by the name 'Queen of Sheba'.

The new *Cimicifuga* plant is a product of a planned breeding program conducted by the Inventor in Hummelo, The Netherlands. The objective of the breeding program was to create new *Cimicifuga* plants with darker-colored leaves and more pendulous racemes.

The new *Cimicifuga* plant originated from a cross-pollination made by the Inventor during the summer of 2007 in Hummelo, The Netherlands, of the *Cimicifuga simplex* 'James Compton', not patented, as the female, or seed, parent with the *Cimicifuga racemosa* 'Changchang', not patented, as the male, or pollen, parent. The new *Cimicifuga* plant was discovered and selected by the Inventor as a single flowering plant within the progeny of the stated cross-pollination in a controlled environment in Hummelo, The Netherlands in the summer of 2008

Asexual reproduction of the new *Cimicifuga* plant by divisions in a controlled environment in Hummelo, The Netherlands since 2008, has shown that the unique features of this new *Cimicifuga* plant are stable and reproduced true to type in successive generations.

SUMMARY OF THE INVENTION

Plants of the new *Cimicifuga* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Queen of Sheba'. These characteristics in combination distinguish 'Queen of Sheba' as a new and distinct cultivar of *Cimicifuga:*

1. Upright and sturdy plant habit.
2. Dark-colored leaves.
3. Freely flowering habit.
4. White-colored flowers arranged on pendulous racemes.
5. Good garden performance.

Plants of the new *Cimicifuga* differ from plants of the female parent, 'James Compton' primarily in leaf coloration as plants of 'James Compton' have much lighter-colored leaves.

Plants of the new *Cimicifuga* differ from plants of the male parent, 'Changchang' primarily in inflorescence orientation as plants of 'Changchang' have less pendulous to upright racemes.

Plants of the new *Cimicifuga* can be compared to plants of *Cimicifuga simplex* 'Brunette', not patented. Plants of the new *Cimicifuga* and 'Brunette' differ primarily in inflorescence orientation as plants of 'Brunette' have upright racemes.

BRIEF DESCRIPTION OF THE PHOTOGRAPHS

The accompanying colored photographs illustrate the overall appearance of the new *Cimicifuga* plant, showing the colors as true as it is reasonably possible to obtain in colored reproductions of this type. Colors in the photographs may differ slightly from the color values cited in the detailed botanical description which accurately describe the colors of the new *Cimicifuga* plant.

The photograph on the first sheet comprises a side perspective view of typical flowering plants of 'Queen of Sheba' grown in an outdoor nursery.

The photograph at the top of the second sheet is a close-up view of a typical inflorescence of 'Queen of Sheba'.

The photograph at the bottom of the second sheet is a close-up view of the upper surface of a typical leaf of 'Queen of Sheba'.

DETAILED BOTANICAL DESCRIPTION

The aforementioned photographs and following observations, measurements and values describe plants grown in containers in Rijpwetering, The Netherlands, under commercial practice in during October in an outdoor nursery with day temperatures ranging from 12° C. to 25° C. and night temperatures ranging from 2° C. to 14° C. Plants had been growing for about one year when the photographs and description were taken. In the following description, color references are made to The Royal Horticultural Society Colour Chart, 2007 Edition, except where general terms of ordinary dictionary significance are used.

Botanical classification: *Cimicifuga simplex*×*Cimicifuga racemosa* 'Queen of Sheba'.

Parentage:

*Female, or seed, parent.*—*Cimicifuga simplex* 'James Compton', not patented.

*Male, or pollen, parent.*—*Cimicifuga racemosa* 'Changchang', not patented.

Propagation:

*Type.*—By divisions.

*Time to produce a rooted plant.*—About one year at 10° C. to 22° C.

*Root description.*—Slightly fibrous; main roots moderately thick, laterals, fine; white to light brown in color.

Plant description:

*Plant form/habit.*—Herbaceous perennial; upright and sturdy plant habit; inverted triangle; flowering stems and leaves basal; dense and bushy growth habit; moderately vigorous to vigorous growth habit; freely and uniformly flowering with numerous flowers on pendulous racemes.

*Growth rate.*—From divisions, about 25 weeks from a rooted young plant are required to produce fully-grown flowering plants.

*Plant height.*—About 144.6 cm.

*Plant width* (*spread*).—About 48.3 cm.

*Stem description.*—Length: About 56.8 cm. Diameter: About 5 mm. Internode length: About 22.5 cm. Strength: Strong. Texture: Sparsely pubescent. Color: Close to N186C and N199B.

Foliage description:

*Arrangement.*—Alternate; ternately compound.

*Leaf length* (*excluding petiole*).—About 26.9 cm.

*Leaf width.*—About 30.1 cm.

*Lateral leaflet length.*—About 6.2 cm.

*Lateral leaflet width.*—About 3.7 cm.

*Terminal leaflet length.*—About 8.6 cm.

*Terminal leaflet width.*—About 5 cm.

*Leaflet shape.*—Elliptic to obovate.

*Leaflet apex.*—Narrowly acute.

*Leaflet base.*—Obtuse to rounded.

*Leaflet margin.*—Serrate.

*Leaflet texture, upper surface.*—Glabrous; slightly rugose.

*Leaflet texture, lower surface.*—Sparsely pubescent.

*Leaflet venation pattern.*—Pinnate.

*Leaflet color.*—Developing leaves, upper surface: Close to N137B. Developing leaves, lower surface: Close to 147B. Fully expanded leaves, upper surface: Close to N186A and 203A; venation, close to N186A and 203A. Fully expanded leaves, lower surface: Close to 148B; venation, close to 152B.

*Leaf petiole length.*—About 20.2 cm.

*Leaf petiole diameter.*—About 3 mm.

*Leaflet petiole length, primary.*—About 7.6 cm.

*Leaflet petiole width, primary.*—About 2 mm.

*Leaflet petiole length, secondary.*—About 3.6 cm.

*Leaflet petiole width, secondary.*—About 1 mm.

*Leaf and leaflet petiole texture, upper and lower surfaces.*—Smooth, glabrous.

*Leaf and leaflet petiole color, upper surface.*—Darker than 152A tinged with close to N199A.

*Leaf and leaflet petiole color, lower surface.*—Close to 152A.

Flower description:

*Flower type/arrangement.*—Numerous single rotate flowers arranged on terminal and axillary racemes; racemes pendulous and elongated; flowers face upright, outward or downward depending on position on the raceme.

*Flowering habit.*—Freely flowering habit with about 60 flowers developing per inflorescence.

*Fragrance.*—None detected.

*Natural flowering season.*—Continuously flowering from September to late October in The Netherlands.

*Postproduction longevity.*—Flowers last about one week on the plant; flowers not persistent.

*Flower buds.*—Height: About 3.5 mm. Diameter: About 3.5 mm. Shape: Globular. Color: Close and N186B to 200B.

*Inflorescence height* (*excluding peduncle*).—About 13.8 cm.

*Inflorescence diameter.*—About 2.6 cm.

*Flower diameter.*—About 1.2 cm.

*Flower depth.*—About 1 cm.

*Petals.*—None observed.

*Sepals.*—Quantity per flower: Typically five in a single whorl. Length: About 5 mm. Lobe width: About 2 mm. Shape: Elliptic. Apex: Obtuse. Margin: Entire. Texture, upper and lower surfaces: Smooth, glabrous. Color, upper two sepals: When opening, upper and lower surfaces: Close to 8B to 8C. Fully opened, upper and lower surfaces: Close to 158D and 155A. Color, lower three sepals: When opening, upper surface: Close to 194D. When opening, lower surface: Close to N186B. Lower three sepals abscise before flowers fully open.

*Peduncles, primary.*—Length: About 83.5 cm. Diameter: About 4 mm. Angle: Erect. Strength: Strong. Texture: Smooth, glabrous. Color: Close to N186C and N199B.

*Peduncles, secondary.*—Length: About 14 cm. Diameter: About 1.5 mm. Angle: About 25° from vertical. Strength: Strong. Texture: Smooth, glabrous. Color: Close to N186C and N199B.

*Pedicels.*—Length: About 2.5 mm. Diameter: About 1 mm. Angle: About 80° from peduncle axis. Strength: Strong. Texture: Smooth, glabrous. Color: Close to N200A.

*Reproductive organs.*—Stamens: Quantity per flower: Typically 30; anthers basifixed. Filament length: About 5 mm. Filament color: Close to N155B to N155C. Anther shape: Broad oval. Anther length: About 0.5 mm. Anther color: Close to NN155A. Pollen amount: Scarce. Pollen color: Close to 155D. Pistils: Quantity per flower: Two. Pistil length: About 2.5 mm. Stigma shape: Pointed. Stigma color: Close to 157D. Style length: About 2 mm. Style color: Close to 157D. Ovary color: Close to 155D.

*Seed/fruit.*—Seed and fruit development have not been observed.

Disease/pest resistance: Plants of the new *Cimicifuga* have not been noted to be resistant to pathogens and pests common to *Cimicifuga*.

Garden performance: Plants of the new *Cimicifuga* have been observed to have good garden performance and tolerate rain and wind. Plants of the new *Cimicifuga* have been observed to be hardy to USDA Zone 5 and to tolerate high temperatures of about 35° C.

It is claimed:

1. A new and distinct *Cimicifuga* plant named 'Queen of Sheba' as illustrated and described.

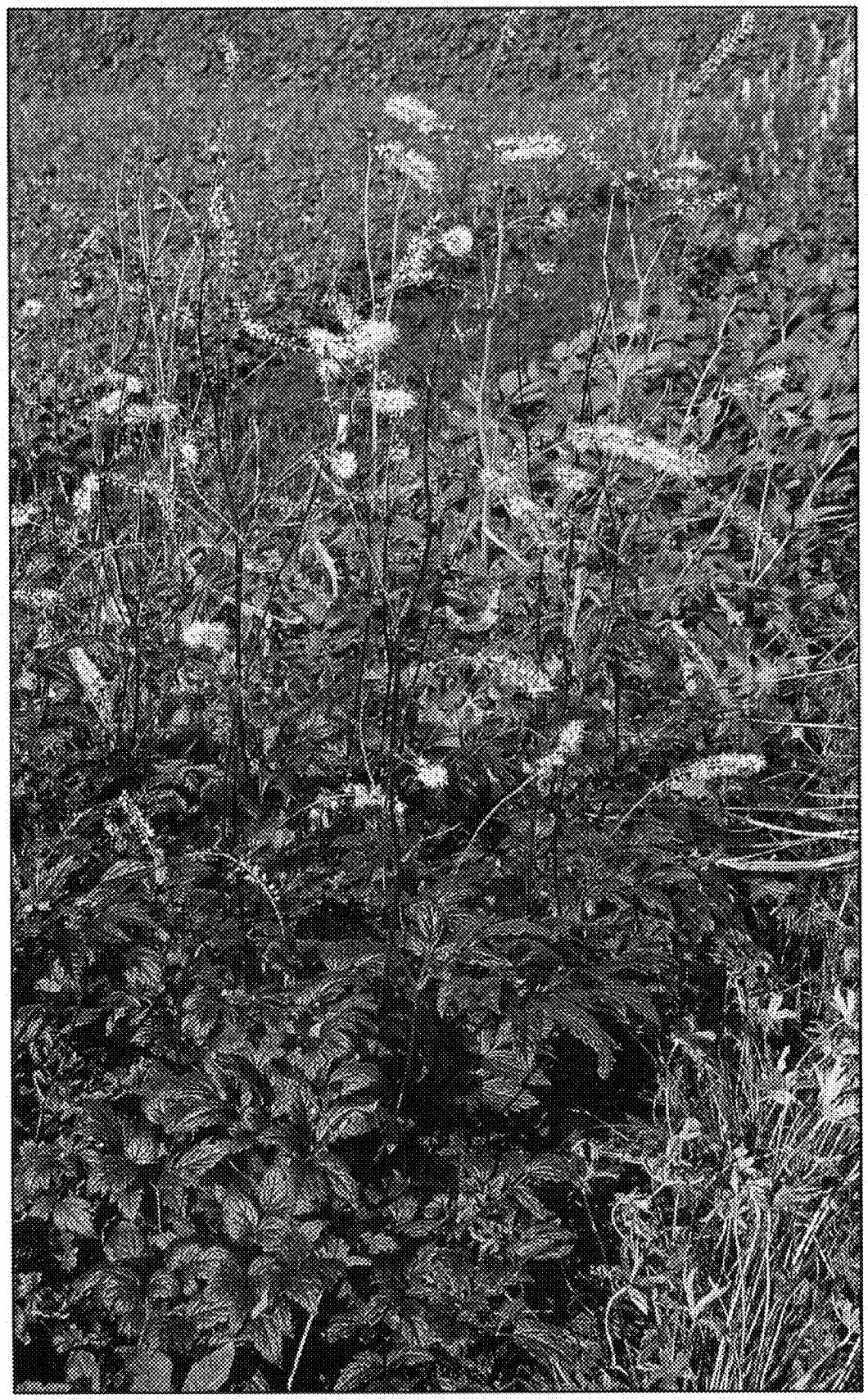

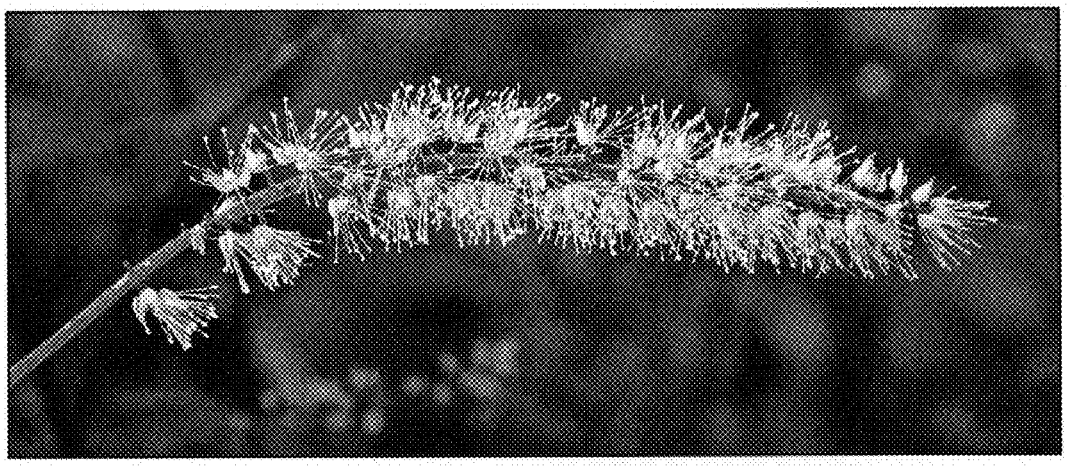
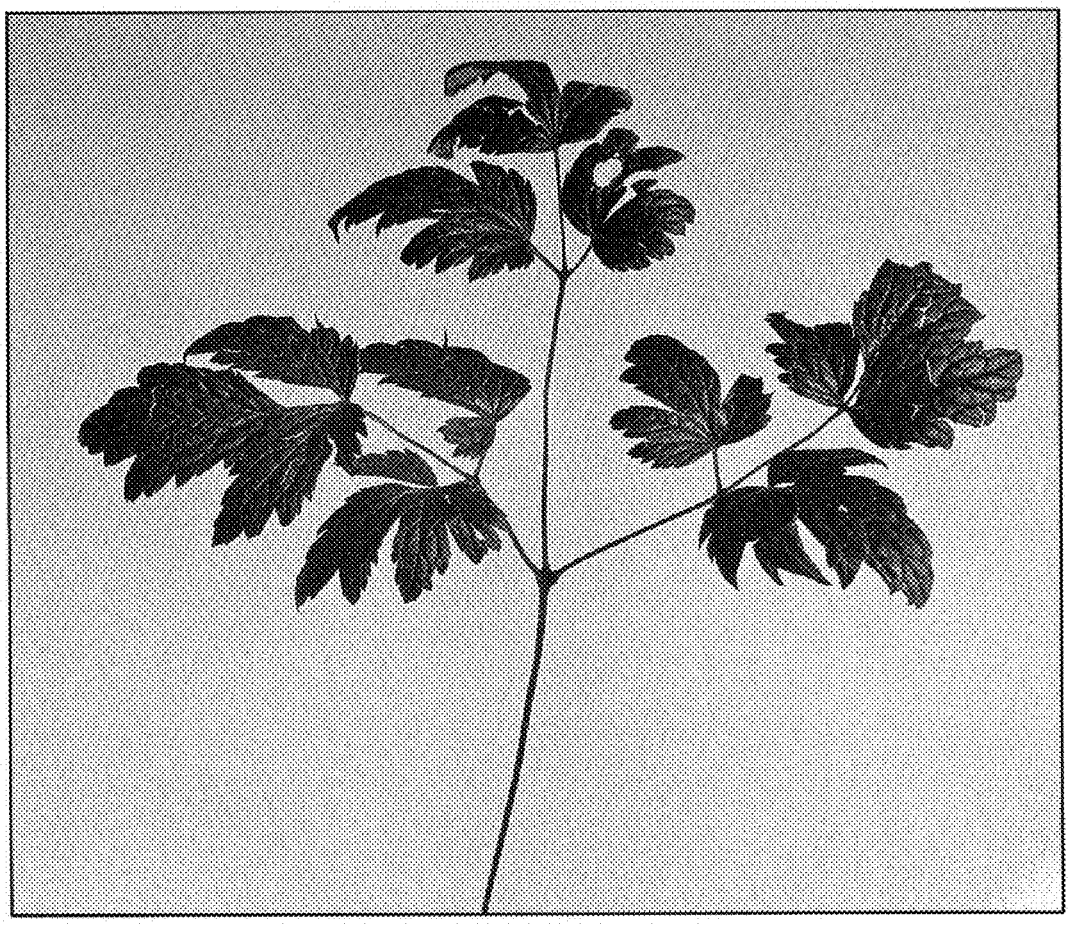

* * * * *